US011927593B2

(12) United States Patent
Sims

(10) Patent No.: US 11,927,593 B2
(45) Date of Patent: Mar. 12, 2024

(54) HIGH-THROUGHPUT SINGLE MOLECULE PROTEIN IDENTIFICATION

(71) Applicant: The Trustees of Columbia University in the City of New York, New York, NY (US)

(72) Inventor: Peter A. Sims, New York, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 969 days.

(21) Appl. No.: 16/592,245

(22) Filed: May 18, 2020

(65) Prior Publication Data
US 2020/0271661 A1    Aug. 27, 2020

Related U.S. Application Data

(62) Division of application No. 15/024,298, filed as application No. PCT/US2014/056731 on Sep. 22, 2014, now Pat. No. 10,466,248.

(60) Provisional application No. 61/881,180, filed on Sep. 23, 2013.

(51) Int. Cl.
*G01N 33/58* (2006.01)
*G01N 33/68* (2006.01)

(52) U.S. Cl.
CPC ....... *G01N 33/6818* (2013.01); *G01N 33/582* (2013.01); *G01N 33/6812* (2013.01); *G01N 2333/95* (2013.01)

(58) Field of Classification Search
CPC ............. G01N 2333/95; G01N 33/582; G01N 33/6812; G01N 33/6818
See application file for complete search history.

(56) References Cited

U.S. PATENT DOCUMENTS

2002/0058273 A1*  5/2002  Shipwash .......... G01N 33/6818
                                                    435/6.12
2005/0164264 A1    7/2005  Shipwash et al.

FOREIGN PATENT DOCUMENTS

WO    WO 2002/012855       2/2002
WO    WO-0221139 A2 *    3/2002    ......... G01N 33/6818

OTHER PUBLICATIONS

Abate et al. "High-throughput injection with microfluidics using picoinjectors", *PNAS* 107:19163. Nov. 9, 2010.
Men et al. "Digital Polymerase Chain Reaction in an Array of Femtoliter Polydimethylsiloxane Microreactors", Analaytical Chemistry, 84:4262. Apr. 7, 2012.
Sims, P. "Multiplexed, Single Molecule Protein Identification for Single Cell Proteomics," Collective IP, Sep. 1, 2013 (Sep. 1, 2013). 5R21EB016980-02. Retrieved from the Intenet :<http://projectreporter.nih.gov/project_description.cfm?projectnumber=1R21EB016980-01> on Dec. 29, 2014 (Dec. 29, 2014). entire document.

(Continued)

*Primary Examiner* — Jennifer Wecker
(74) *Attorney, Agent, or Firm* — Casimir Jones, S.C.; Rikki A. Hullinger

(57) ABSTRACT

The present invention is methods and assays for identifying single proteins from a sample, without the use of affinity reagents. The methods and assays combine endopeptidase-based component of conventional peptide mapping with single molecule labeling and a microreactor array platform. The invention also includes kits for performing the methods and assays.

19 Claims, 9 Drawing Sheets

Specification includes a Sequence Listing.

(56) References Cited

OTHER PUBLICATIONS

Baker, M. "Single-molecule studies lead to high-throughput sequencing." Nature Methods, Jul. 1, 2011 (Jul. 1, 2011), vol. 8, No. 7, p. 523. entire document.

Sims et al. "Fluorogenic DNA sequencing in PDMS microreactors," Nature Methods, Jun. 12, 2011 (Jun. 12, 2011), vol. 8, pp. 575-580. entire document.

* cited by examiner

Control Beads (no GluC) after 285 mins    GluC-exposed Beads after 285 mins

Figure 7A
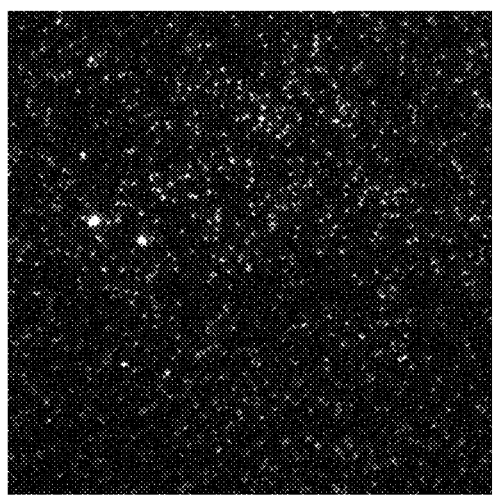
Figure 7B
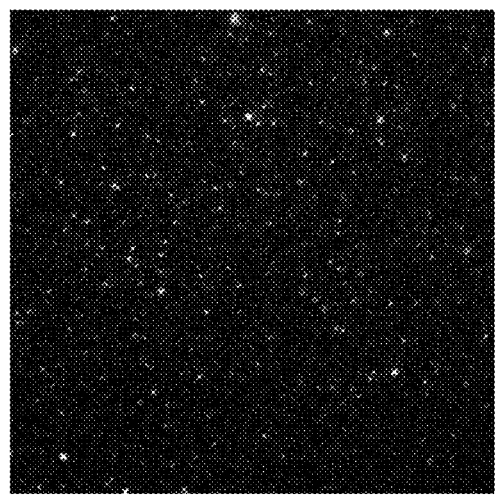
Figure 7C
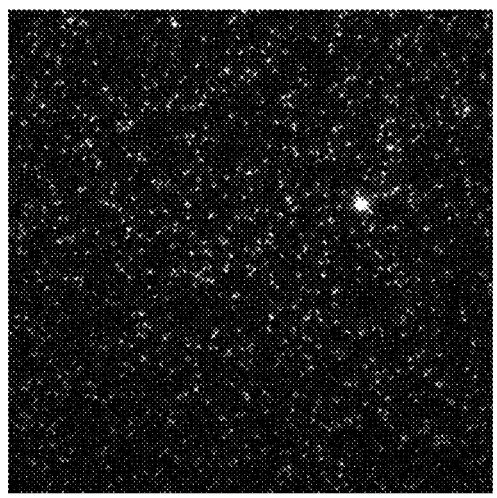
Figure 7D
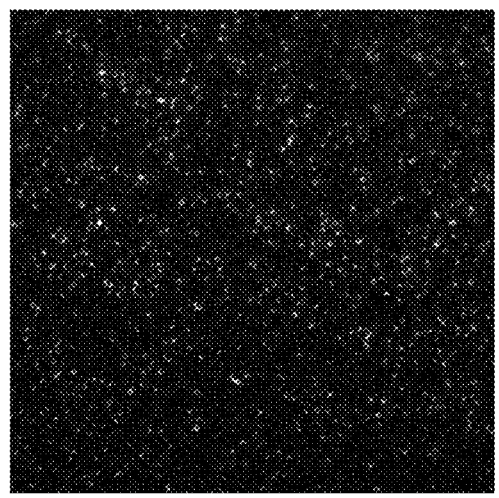
Figure 7

SEQUENCE LISTING

```
<160> NUMBER OF SEQ ID NOS: 7

<210> SEQ ID NO 1
<211> LENGTH: 18
<212> TYPE: PRT
<213> ORGANISM: Homo sapiens

<400> SEQUENCE: 1

Asn Gly Ile Glu Gly Leu Ala Val Lys Ile Ala Val Asp Leu Asn Ala
1               5                   10                  15

Cys Arg

<210> SEQ ID NO 2
<211> LENGTH: 12
<212> TYPE: PRT
<213> ORGANISM: Homo sapiens

<400> SEQUENCE: 2

Asn Gly Ile Glu Gly Leu Ala Val Lys Ile Ala Val
1               5                   10

<210> SEQ ID NO 3
<211> LENGTH: 28
<212> TYPE: PRT
<213> ORGANISM: Homo sapiens

<400> SEQUENCE: 3
```

```
Gly Ser Arg Ser Leu Ala Gly Lys Ala Ser Ala Ala Glu Gly Ala Ala
1               5                   10                  15

Ser Ala Cys Gly Ser Gly His His His His His His
            20                  25

<210> SEQ ID NO 4
<211> LENGTH: 28
<212> TYPE: PRT
<213> ORGANISM: Homo sapiens

<400> SEQUENCE: 4

Gly Ser Arg Ser Leu Ala Gly Lys Ala Ser Ala Ala Glu Gly Ala Ala
1               5                   10                  15

Ser Ala Lys Gly Ser Gly His His His His His His
            20                  25

<210> SEQ ID NO 5
<211> LENGTH: 28
<212> TYPE: PRT
<213> ORGANISM: Homo sapiens

<400> SEQUENCE: 5

Gly Ser Arg Ser Leu Ala Gly Lys Ala Ser Ala Ala Glu Gly Ala Ala
1               5                   10                  15

Ser Ala Cys Gly Ser Gly His His His His His His
            20                  25

<210> SEQ ID NO 6
<211> LENGTH: 13
<212> TYPE: PRT
<213> ORGANISM: Homo sapiens

<400> SEQUENCE: 6

Gly Ser Arg Ser Leu Ala Gly Lys Ala Ser Ala Ala Glu
1               5                   10

<210> SEQ ID NO 7
<211> LENGTH: 15
<212> TYPE: PRT
<213> ORGANISM: Homo sapiens

<400> SEQUENCE: 7

Gly Ala Ala Ser Ala Cys Gly Ser Gly His His His His His His
1               5                   10                  15
```

HIGH-THROUGHPUT SINGLE MOLECULE PROTEIN IDENTIFICATION

CROSS-REFERENCE TO RELATED APPLICATIONS

The present application is a divisional of U.S. patent application Ser. No. 15/024,298, filed Mar. 23, 2016, which is a U.S. National Phase Application under 35 U.S.C. § 371 of International Patent Application No. PCT/US2014/056731, filed Sep. 22, 2014, which claims priority to U.S. patent application Ser. No. 61/881,180 filed Sep. 23, 2013, the disclosures of all of which are hereby incorporated by reference in their entireties. The International Application was published in English on Mar. 26, 2015 as WO 2015/042506.

This invention was made with government support under grants 1R21EB016980 and 1K01EB016071 awarded by NIH. The government has certain rights in the invention.

FIELD OF THE INVENTION

This invention relates to the field of methods and assays for protein identification at the single molecule level without affinity reagents.

BACKGROUND OF THE INVENTION

Single cell and low input proteomics represent major challenges and opportunities for biomedical technology development. Even in bulk studies, assays such as microarray expression profiling are frequently substituted for protein-level characterization due to the technical complexity inherent to proteomics. Although unbiased nucleic acid analysis (e.g. transcriptomics) is essential to a complete molecular description of any biological system, a quantitative handle on protein abundance and modification is an absolute requirement for defining complex cellular phenotypes.

Current proteomic technologies fall into two basic categories: 1) high-sensitivity approaches that require the use of affinity reagents, such as antibodies; and 2) low-sensitivity protein identification by mass spectrometry (MS).

This new method bridges this gap by providing protein identification with single molecule sensitivity without the use of affinity reagents like antibodies.

SUMMARY OF THE INVENTION

The present invention is based upon the surprising discovery that by combining the endopeptidase-based upstream component of conventional "bottom-up" proteomics with single molecule fluorescence microscopy and a microfabricated array platform, single proteins can be easily and specifically identified without the use of affinity reagents.

One embodiment of the present invention is a method for identifying a single protein in a sample, comprising:
 A. introducing the protein into a microreactor chamber, at a concentration that results in a single protein molecule in the microreactor chamber, and wherein the microreactor chamber contains an endopeptidase, and an amine-reactive surface to which the microreactor chamber is sealed;
 B. allowing the endopeptidase to digest the protein into peptides;
 C. allowing the peptides to react with the amine-reactive surface, resulting in the peptides attaching in a cluster on the amine-reactive surface, wherein the cluster is associated with the single protein molecule;
 D. labeling the peptides at specific amino acid residues such that the specific amino acid residues can be detected when imaged;
 E. imaging the peptides to detect the labeled amino acids and generate amino acid sequences;
 F. digesting the peptides with enzymes or chemicals that digest the peptides at specific amino acid residues and imaging the resulting peptides to generate further amino acid sequences;
 G. comparing the generated amino acid sequences of the peptides from the single protein molecule with known amino acid sequences of proteins; and
 H. identifying the protein from the comparison in step (G).

A further embodiment of the present invention is an assay for identifying a single protein in a sample, comprising:
 A. introducing the protein into a microreactor chamber, at a concentration that results in a single protein molecule in the microreactor chamber, and wherein the microreactor chamber contains an endopeptidase, and an amine-reactive surface to which the microreactor chamber is sealed;
 B. allowing the endopeptidase to digest the protein into peptides;
 C. allowing the peptides to react with the amine-reactive surface, resulting in the peptides attaching in a cluster on the amine-reactive surface, wherein the cluster is associated with the single protein molecule;
 D. labeling the peptides at specific amino acid residues such that the specific amino acid residues can be detected when imaged;
 E. imaging the peptides to detect the labeled amino acids and generate amino acid sequences;
 F. digesting the peptides with enzymes or chemicals that digest the peptides at specific amino acid residues and imaging the resulting peptides to generate additional amino acid sequences;
 G. comparing the generated amino acid sequences of the peptides from the single protein molecule with known amino acid sequences of proteins; and
 H. identifying the protein from the comparison in step (G).

A further embodiment of the present invention is a method for identifying a single protein in a sample, comprising:
 A. labeling the protein at specific amino acid residues such that the specific amino acid residues can be detected when imaged;
 B. introducing the protein into a microreactor chamber, at a concentration that results in a single protein molecule in the microreactor chamber, and wherein the microreactor chamber contains an endopeptidase, and an amine-reactive surface to which the microreactor chamber is sealed;
 C. allowing the endopeptidase to digest the protein into peptides;
 D. allowing the peptides to react with the amine-reactive surface, resulting in the peptides attaching in a cluster on the amine-reactive surface, wherein the cluster is associated with the single protein molecule;
 E. imaging the peptides to detect labeled amino acids and generate amino acid sequences;

F. digesting the peptides with enzymes or chemicals that digest the peptides at specific amino acid residues and imaging the resulting peptides to generate additional amino acid sequences;

G. comparing the generated amino acid sequences of the peptides from the single protein molecule with known amino acid sequences of proteins; and H. identifying the protein from the comparison in step (G).

Yet a further embodiment of the present invention is an assay for identifying a single protein in a sample, comprising:

A. labeling the protein at specific amino acid residues such that the specific amino acid residues can be detected when imaged;

B. introducing the protein into a microreactor chamber, at a concentration that results in a single protein molecule in the microreactor chamber, and wherein the microreactor chamber contains an endopeptidase, and an amine-reactive surface to which the microreactor chamber is sealed;

C. allowing the endopeptidase to digest the protein into peptides;

D. allowing the peptides to react with the amine-reactive surface, resulting in the peptides attaching in a cluster on the amine-reactive surface, wherein the cluster is associated with the single protein molecule;

E. imaging the peptides to detect labeled amino acids and generate amino acid sequences;

F. digesting the peptides with enzymes or chemicals that digest the peptides at specific amino acid residues and imaging the resulting peptides to generate additional amino acid sequences;

G. comparing the generated amino acid sequences of the peptides from the single protein molecule with known amino acid sequence of proteins; and H. identifying the protein from the comparison in step (G).

Another embodiment of the present invention is a method for identifying several single proteins in a sample, comprising:

A. introducing the proteins into microreactor chambers contained in array, at a concentration that results in a single protein molecule in each microreactor chamber, and wherein each microreactor chamber contains an endopeptidase, and an amine-reactive surface to which all of the microreactor chambers in the array are sealed;

B. allowing the endopeptidase to digest the proteins into peptides;

C. allowing the peptides to react with the amine-reactive surface, resulting in the peptides attaching in a cluster on the amine-reactive surface, wherein the cluster is associated with the single protein molecule, and the arrangement of the clusters on the amine-reactive surface of the array forms a recognizable pattern;

D. labeling the peptides at specific amino acid residues such that the specific amino acid residues can be detected when imaged;

E. imaging the peptides to detect the labeled amino acids and generate amino acid sequences;

F. digesting the peptides with enzymes or chemicals that digest the peptides at specific amino acid residues and imaging the resulting peptides to generate additional amino acid sequences;

G. comparing the generated amino acid sequences of the peptides from the single protein molecules with known amino acid sequences of proteins; and H. identifying the proteins from the comparison in step (G).

Another embodiment of the present invention is an assay for identifying several single proteins in a sample, comprising:

A. introducing the proteins into microreactor chambers contained in array, at a concentration that results in a single protein molecule in each microreactor chamber, and wherein each microreactor chamber contains an endopeptidase, and an amine-reactive surface to which all of the microreactor chambers in the array are sealed;

B. allowing the endopeptidase to digest the proteins into peptides;

C. allowing the peptides to react with the amine-reactive surface, resulting in the peptides attaching in a cluster on the amine-reactive surface, wherein the cluster is associated with the single protein molecule, and the arrangement of the clusters on the amine-reactive surface of the array forms a recognizable pattern;

D. labeling the peptides at specific amino acid residues such that the specific amino acid residues can be detected when imaged;

E. imaging the peptides to detect the labeled amino acids and generate amino acid sequences;

F. digesting the peptides with enzymes or chemicals that digest the peptides at specific amino acid residues and imaging the resulting peptides to generate additional amino acid sequences;

G. comparing the generated amino acid sequences of the peptides from the single protein molecules with known amino acid sequences of proteins; and H. identifying the proteins from the comparison in step (G).

Another embodiment of the present invention is a method for identifying several single proteins in a sample, comprising:

A. labeling the proteins at specific amino acid residues such that the specific amino acid residues can be detected when imaged;

B. introducing the proteins into microreactor chambers contained in array, at a concentration that results in a single protein molecule in each microreactor chamber, and wherein each microreactor chamber contains an endopeptidase, and an amine-reactive surface to which all of the microreactor chambers in the array are sealed;

C. allowing the endopeptidase to digest the proteins into peptides;

D. allowing the peptides to react with the amine-reactive surface, resulting in the peptides attaching in a cluster on the amine-reactive surface, wherein the cluster is associated with the single protein molecule, and the arrangement of the clusters on the amine-reactive surface of the array forms a recognizable pattern;

E. imaging the peptides to detect the labeled amino acids and generate amino acid sequences;

F. digesting the peptides with enzymes or chemicals that digest the peptides at specific amino acid residues and imaging the resulting peptides to generate additional amino acid sequences;

G. comparing the generated amino acid sequences of the peptides from the single protein molecules with known amino acid sequences of proteins; and H. identifying the proteins from the comparison in step (G).

Another embodiment of the present invention is an assay for identifying several single proteins in a sample, comprising:

A. labeling the proteins at specific amino acid residues such that the specific amino acid residues can be detected when imaged;
B. introducing the proteins into microreactor chambers contained in array, at a concentration that results in a single protein molecule in each microreactor chamber, and wherein each microreactor chamber contains an endopeptidase, and an amine-reactive surface to which all of the microreactor chambers in the array are scaled;
C. allowing the endopeptidase to digest the proteins into peptides;
D. allowing the peptides to react with the amine-reactive surface, resulting in the peptides attaching in a cluster on the amine-reactive surface, wherein the cluster is associated with the single protein molecule, and the arrangement of the clusters on the amine-reactive surface of the array forms a recognizable pattern;
E. imaging the peptides to detect the labeled amino acids and generate amino acid sequences;
F. digesting the peptides with enzymes or chemicals that digest the peptides at specific amino acid residues and imaging the resulting peptides to generate amino acid sequences;
G. comparing the generated amino acid sequences of the peptides from the single protein molecules with known amino acid sequences of proteins; and
H. identifying the proteins from the comparison in step (G).

Another embodiment of the present invention is a method for identifying a single protein in a sample, comprising:
A. introducing the protein onto a bead, at a concentration resulting in a single protein molecule on the bead, and wherein the bead contains an amine-reactive surface;
B. introducing an endopeptidase to the bead to digest the protein into peptides;
C. allowing the peptides to react with the amine-reactive surface, resulting in the peptides attaching in a cluster on the amine-reactive surface, wherein the cluster is associated with the single protein molecule;
D. labeling the peptides at specific amino acid residues such that the specific amino acid residues can be detected when imaged;
E. imaging the peptides to detect the labeled amino acids and generate amino acid sequences;
F. digesting the peptides with enzymes or chemicals that digest the peptides at specific amino acid residues and imaging the resulting peptides to generate additional amino acid sequences;
G. comparing the generated amino acid sequences of the peptides from the single protein molecule with known amino acid sequences of proteins; and
H. identifying the protein from the comparison in step (G).

Another embodiment of the present invention is an assay for identifying a single protein in a sample, comprising:
A. introducing the protein onto a bead, at a concentration that results in a single protein molecule on the bead, and wherein the bead contains an amine-reactive surface;
B. introducing an endopeptidase to the bead to digest the protein into peptides;
C. allowing the peptides to react with the amine-reactive surface, resulting in the peptides attaching in a cluster on the amine-reactive surface, wherein the cluster is associated with the single protein molecule;
D. labeling the peptides at specific amino acid residues such that the specific amino acid residues can be detected when imaged;
E. imaging the peptides to detect the labeled amino acids and generate amino acid sequences;
F. digesting the peptides with enzymes or chemicals that digest the peptides at specific amino acid residues and imaging the resulting peptides to generate additional amino acid sequences;
G. comparing the generated amino acid sequences of the peptides from the single protein molecule with known amino acid sequences of proteins; and
H. identifying the protein from the comparison in step (G).

A further embodiment is a method for identifying a single protein in a sample, comprising:
A. labeling the protein at specific amino acid residues such that the specific amino acid residues can be detected when imaged;
B. introducing the protein onto a bead, at a concentration that results in a single protein molecule on the bead, and wherein the bead contains an amine-reactive surface;
C. introducing an endopeptidase to the bead to digest the protein into peptides;
D. allowing the peptides to react with the amino-reactive surface, resulting in the peptides attaching in a cluster on the amine-reactive surface, wherein the cluster is associated with the single protein molecule;
E. imaging the peptides to detect labeled amino acids and generate amino acid sequences;
F. digesting the peptides with enzymes or chemicals that digest the peptides at specific amino acid residues and imaging the resulting peptides to generate additional amino acid sequences;
G. comparing the generated amino acid sequences of the peptides from the single protein molecule with known amino acid sequences of proteins; and
H. identifying the protein from the comparison in step (G).

A further embodiment is an assay for identifying a single protein in a sample, comprising:
A. labeling the protein at specific amino acid residues such that the specific amino acid residues can be detected when imaged;
B. introducing the protein onto a bead, at a concentration that results in a single protein molecule on the bead, and wherein the bead contains an amine-reactive surface;
C. introducing an endopeptidase to the bead to digest the protein into peptides;
D. allowing the peptides to react with the amine-reactive surface, resulting in the peptides attaching in a cluster on the amine-reactive surface, wherein the cluster is associated with the single protein molecule;
E. imaging the peptides to detect labeled amino acids and generate amino acid sequences;
F. digesting the peptides with enzymes or chemicals that digest the peptides at specific amino acid residues and imaging the resulting peptides to generate additional amino acid sequences;
G. comparing the generated amino acid sequences of the peptides from the single protein molecule with known amino acid sequences of proteins; and
H. identifying the protein from the comparison in step (G).

The methods and assays of the present invention can be used for diagnostic purposes, by a diagnostic laboratory, and/or a health care provider.

The sample from which the protein is obtained can be from any biological tissue or bodily fluid. The protein can be obtained and processed from the biological tissue or bodily fluid by any method known in the art, in order to obtain a purified and/or isolated protein sample.

The sample from which the protein is obtained can also be a drug in development. The method is also useful in basic research and proteomic studies.

The microreactive chamber can be made of any elastomeric material. The preferred material is polydimethylsiloxane (PDMS).

Any endopeptidase can be used in the microreactor chamber with trypsin being the preferred endopeptidase.

The amine-reactive surface can be made out of any material but glass is preferred. The surface is coated with an amine-reactive substance including but not limited to aldehyde- or N-hydroxysuccinimide (NHS) silane.

A reaction mixture may be added to the microreactor chamber or the bead with the protein or, before or after introducing the protein into the microreactor chamber or bead. The reaction mixture can comprise a denaturant, reagents for facilitating the coupling of the peptides to the amine-reactive surface, and amine-blocked, autolysis-resistant trypsin or other endopeptidases.

The protein or peptides must be labeled in order to be visualized. Moreover, the protein or peptides must be labeled at specific amino acid residues in order to be useful in the method. This is accomplished by methods known in the art.

The peptides generated from the first digestion can be digested further in order to obtain further amino acid sequence information. This step is accomplished by adding enzymes and/or chemicals that digest the peptides at particular amino acid residues. This step of the method or assay can be performed once, or several times.

Yet another embodiment of the present invention is a kit for identifying single proteins in a sample comprising an array comprising microreactor chambers coated with an endopeptidase, an amine-reactive surface material that is capable of sealing to the array, reagents for labeling the amino acids such as fluorescent dyes or affinity tags, endopeptidases, and instructions for use.

The kit can further comprise denaturants, buffers, and reagents for coupling the peptides to the amine-reactive surface, and an amine-blocked, autolysis-resistant endopeptidase.

A further embodiment of the present invention is a kit for identifying single proteins in a sample comprising beads, with an amine-reactive surface, reagents for labeling the amino acids such as fluorescent dyes or affinity tags, endopeptidases, and instructions for use.

The kit can further comprise denaturants, buffers, and reagents for coupling the peptides to the beads, and an amine-blocked, autolysis-resistant endopeptidase.

BRIEF DESCRIPTION OF THE FIGURES

For the purpose of illustrating the invention, there are depicted in drawings certain embodiments of the invention. However, the invention is not limited to the precise arrangements and instrumentalities of the embodiments depicted in the drawings.

FIG. 7 shows representative fluorescence images of individual peptide molecules on the glass capture surfaces. FIG. 7A shows prior to introduction of GluC enzyme, and FIG. 7B shows after incubation with the GluC enzyme. Note that the density of fluorescent molecules on the surface is significantly diminished. FIG. 7C shows a control flow cell to which GluC is not introduced prior to incubation, in the absence of GluC, and FIG. 7D shows the control flow cell after incubation in the absence of GluC. Note that the surface densities in FIGS. 6C and 6D are similar.

DETAILED DESCRIPTION OF THE INVENTION

Figure 1:
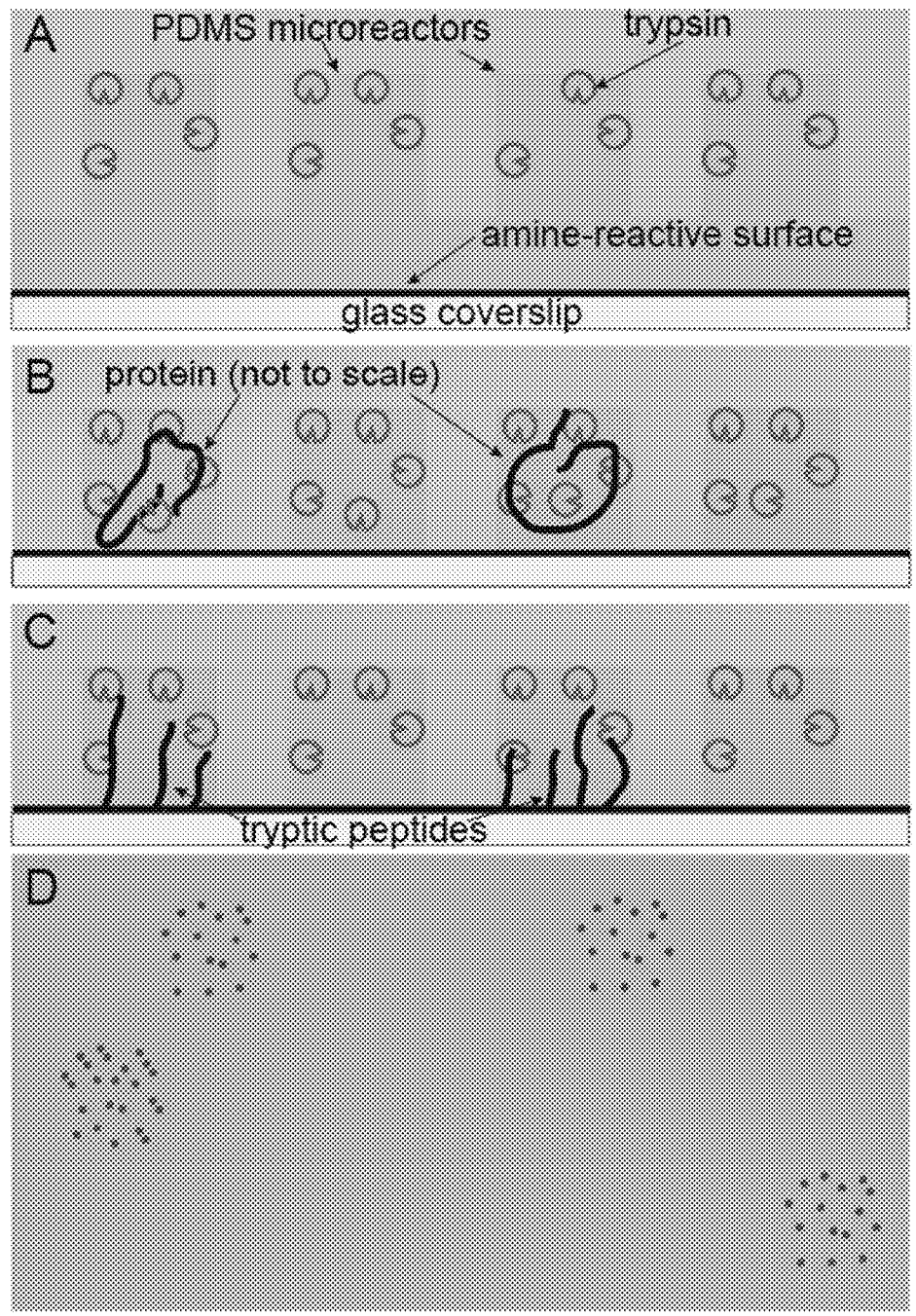
FIG. 1 is a schematic of peptide cluster generation.

Numerous biological problems ranging from whole proteome analysis to gene-specific studies of protein-protein interaction complexes require protein identification, without a priori knowledge of the target proteins involved. Peptide mapping by mass spectrometry (peptide mass fingerprinting) is used in protein characterization to produce a unique "fingerprint" of an individual protein and to compare this with the theoretical gene-derived amino acid sequence. However, many desirable applications including single cell studies and analysis of small clinical specimens do not involve sufficient input material to utilize mass spectrometry effectively.

To address these challenges, this invention combines the endopeptidase-based upstream component of conventional peptide mapping with single molecule fluorescence microscopy and a microfabricated array platform. Capitalizing on the amino acid specificity of reactive fluorescent dyes, affinity tags, and endopeptidases, the sequence information from single peptide molecules produced by tryptic digest can be obtained. Amino acid-specific labels before and after amino acid-specific cleavage by endopeptidases using a fluorescence microscope for single molecule detection are read. However, to be useful this information must be associated with the protein molecules from which the peptides are derived. Thus, a unique system was developed, to trap single protein molecules in individual, reversibly sealable microreactors prior to digestion and capture the resulting tryptic peptides in clusters on the functionalized lower surface of each microreactor.

As shown in the Examples, several experiments using singly- and dual-labeled proteins and peptides to demonstrate the feasibility of this approach. Both solution-phase and solid-phase bulk experiments demonstrated detection of sequence-specific peptide digestion.

Definitions

The terms used in this specification generally have their ordinary meanings in the art, within the context of this invention and the specific context where each term is used. Certain terms are discussed below, or elsewhere in the specification, to provide additional guidance to the practitioner in describing the methods of the invention and how to use them. Moreover, it will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of the other synonyms. The use of examples anywhere n the specification, including examples of any terms discussed herein, is illustrative only, and in no way limits the scope and meaning of the invention or any exemplified term. Likewise, the invention is not limited to its preferred embodiments.

The term "amino acid," includes the residues of the natural amino acids (e.g. Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D or L form, as well as unnatural amino acids (e.g. phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, alpha-methylalanine, para-benzoylphenylalanine, phenylglycine, propargylglycine, sarcosine, and tert-butylglycine). The term also includes natural and unnatural amino acids bearing a conventional amino protecting group (e.g. acetyl or benzyloxycarbonyl), as well as natural and unnatural amino acids protected at the carboxy terminus (e.g. as a $(C_1-C_6)$alkyl, phenyl or benzyl ester or amide).

The term "peptide" includes any sequence of two or more amino acids. Peptide sequences specifically recited herein are written with the amino terminus on the left and the carboxy terminus on the left.

The term "microreactor" and the like refers to a device in which a reaction takes place in a confinement with a dimension of less than about 1 mm in diameter.

As used herein, the term "isolated" and the like means that the referenced material is free of components found in the natural environment in which the material is normally found.

In particular, isolated biological material is free of cellular components. An isolated protein may be associated with other proteins or nucleic acids, or both, with which it associates in the cell, or with cellular membranes if it is a membrane-associated protein. An isolated material may be, but need not be, purified.

The term "purified" and the like as used herein refers to material that has been isolated under conditions that reduce or eliminate unrelated materials, i.e., contaminants.

Microfabricated Array Platform

Similar to mass spectrometry, the method of the current invention for protein identification starts by digesting the protein with trypsin or another endopeptidase. In order to associate the peptides resulting from the tryptic or other endopeptidase digestion of the protein with the originating protein molecule, the peptides must be immobilized in localized clusters. It was discovered that this could be accomplished by using reversibly sealable microreactors.

Single protein molecules are placed or trapped into individual chambers of a reversibly, sealable microreactor. This can be accomplished by diluting a protein solution to a concentration such that nearly every microreactor chamber contains either zero or one molecule. This can be determined by one of skill in the art, and will depend on the volume of the individual microreactor chambers. See Men et al. (2012).

Microreactors can be made from any material that is elastomeric in nature or that can otherwise be sealed. These materials include but are not limited to polydimethylsiloxane (PDMS), glass, agarose, polymethylmethacrylate (PMMA), and silicon. PDMS is the preferred material since the microreactor system can be constructed reproducibly and inexpensively using this material. While PDMS is sufficiently elastomeric that microreactors fabricated in PDMS can be sealed mechanically by contacting them with a flat surface, there are alternative approaches to sealing microreactors that do not require this elastomeric property. For example, microreactors can be sealed by flowing water-immiscible oil over microreactors containing an aqueous solution. See U.S. patent application Ser. No. 13/498,072.

A preferred microarray system comprises an array of about 5-100 micron diameter chambers fabricated in a slab of flexible and transparent material. Each array can have about 100 to 1,000,000,000 chambers. Also because of the elastomeric nature of the material, the chambers can be pressed against a glass coverslip and sealed, which isolates the contents of each chamber.

A further embodiment of the invention is the use of latex or silica beads. In this case, the surface chemistry for capturing peptides is on a bead which can be deposited either in microwells or enclosed in a water-oil emulsion droplet. In the case that the beads are deposited in microwells, proteins can be introduced and trapped by sealing the microwells as described above. In the case that the beads are enclosed in a water-oil emulsion droplet, various microfluidic devices have been reported for controlled droplet generation, droplet manipulation, and for injecting materials such as proteins into droplets (Abate et al. (2010); U.S. Pat. No. 8,765,485).

Preferably, the inner walls of the microreactors are covalently coated with an endopeptidase, to generate peptide fragments. Endopeptidases that can be used include but are not limited to trypsin, chymotrypsin, elastase, thermolysin, pepsin, clostripan, glutamyl endopeptidase (GluC), ArgC, peptidyl-asp endopeptidase (ApsN), endopeptidase LysC and endopeptidase LysN. Trypsin is preferred.

The surface to which the microreactors are scaled is preferentially made of glass and is coated with an amine-reactive surface, including but not limited to aldehyde- or N-hydroxysuccinimide (NHS) silane, tetraflurophenyl (TFP) ester, silane, isocyanate silane, and epoxy silane. In the alternative, a latex or silicon bead can contain an amine-reactive surface.

In some embodiments, lysines in target proteins are pre-blocked with a reactive acetylating reagent prior to trypsinization to prevent them from reacting with the surface. Certain acetylating reagents allow subsequent reactions to take place at the blocked residue.

A reaction mixture can also be added to each microreactor chamber or bead with the protein, or before or after the protein is introduced or placed into the microreactor chamber or bead. The reaction mixture may contain a denaturant (to which trypsin is resistant), appropriate reagents for coupling the resultant peptides to the amine-reactive surface, such as a mild reductant like sodium cyanoborohydride in the case of an aldehyde surface, and amine-blocked, autolysis-resistant trypsin or other endopeptidases.

As the endopeptidase, e.g., trypsin, digests the protein in the sealed microreactors, the resultant peptides diffuse and react with the lower surface of the microreactor at their N-termini, generating an array of well-separated peptide clusters. Each peptide cluster is associated with an original protein molecule.

This peptide cluster generation is a novel and critical aspect of the current invention and is shown schematically in FIG. 1. FIG. 1A depicts the microreactors coated with trypsin held over an amine-reactive surface; FIG. 1B shows that the single protein molecules are loaded into each microreactor chamber, which are then scaled; FIG. 1C shows that trypsinization occurs resulting in N-terminal immobilization of tryptic peptides to the amine-reactive surface; and FIG. 1D shows the results: clusters of microscopically resolvable tryptic peptides, each corresponding to one protein molecule, patterned on the amine-reactive surface of each microreactor chamber.

Figure 2A:
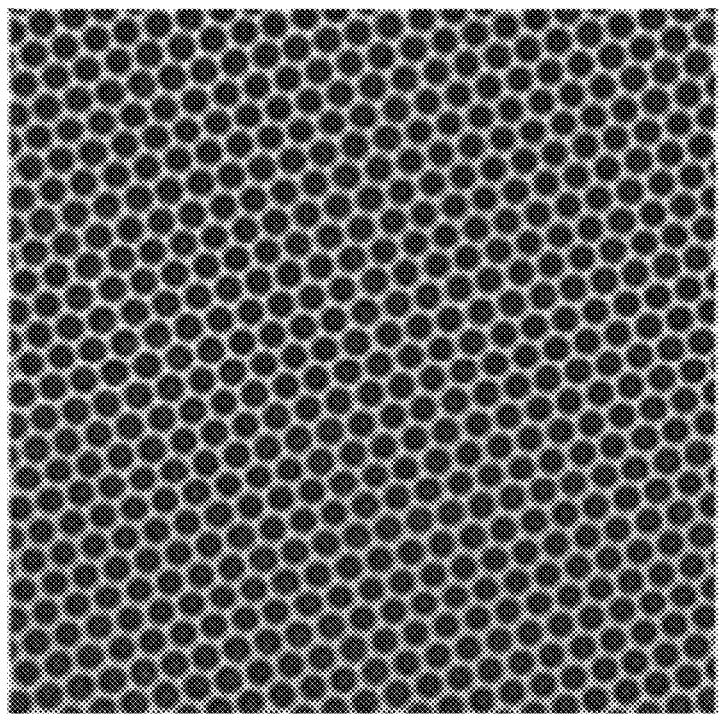
FIG. 2A depicts bright field image of a PDMS microwell array containing five micron-diameter microwells.
Figure 2B:
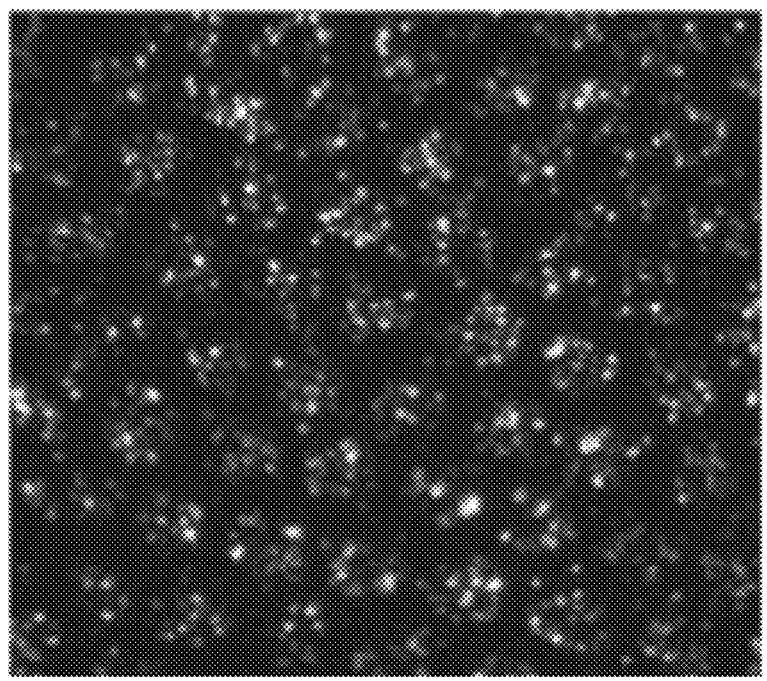
FIG. 2B depicts the fluorescence image of a functionalized glass capture surface after trapping fluorescently labeled protein molecules in the microwells, digesting them with trypsin, and capturing the resultant tryptic peptides in a defined spatial pattern on the surface.

As shown in FIG. 2A, a microfluidic system and compatible surface chemistry for trapping protein molecules in micron-scale wells has been developed, digesting the trapped molecules with trypsin, and capturing the resultant tryptic peptides covalently on a glass surface. The glass coverslip is silanized with an aldehyde-functionalized silane that allows a direct reaction between the surface and the N-termini of tryptic peptides. FIG. 2B shows that fluorescently-labeled tryptic peptides can be patterned on the functionalized glass surface in spatially defined circles using this device and individual, labeled peptide molecules can be resolved within these circular patterns.

Generating Sequence Information

Once the tryptic peptides associated with each target protein molecule are clustered on a surface, sequence information from the individual peptides is obtained.

Figure 3:
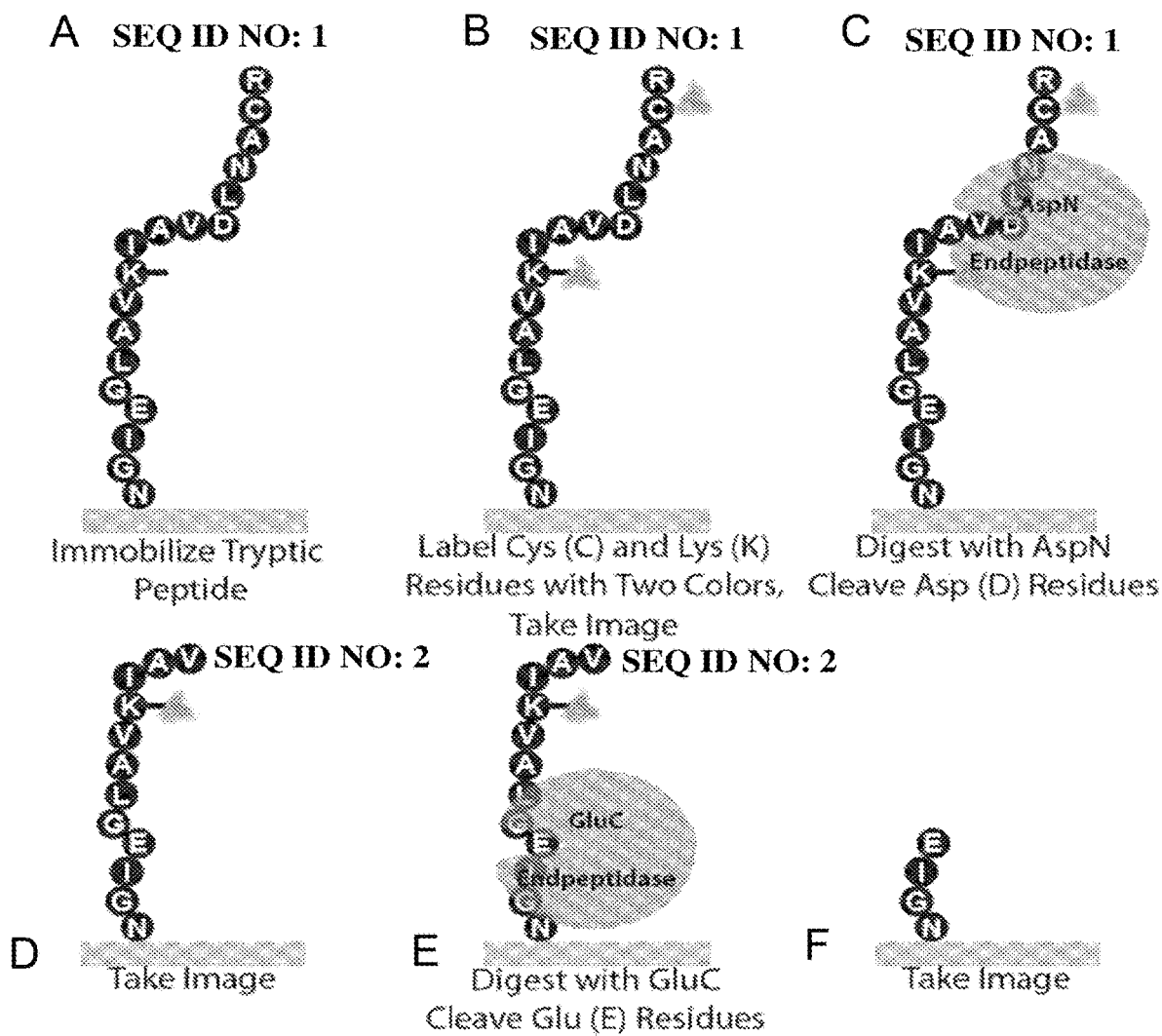
FIG. 3 is a schematic depicting the obtention of course-grained sequence information from individual peptide molecules via residue-specific labels and endopeptidases.

One approach is a so-called coarse-grained approach as illustrated schematically in FIG. 3. The proteins that were originally trapped and digested in the microwells can be labeled with fluorescent dyes prior to introducing them to the device, or in the alternative, the peptides that result from the initial endopeptidase, i.e., trypsin, digestion can be labeled after they have been captured on the surface.

Any fluorescent dye known to one of skill in the art can be used in the present invention. A fluorescent dye can be excited to fluoresce by exposure to a certain wavelength of light. Preferred fluorescent groups include molecules that are capable of absorbing radiation at one wavelength and emitting radiation at a longer wavelength.

These would include tetramethylrhodamine-maleimide as well as Alexa Fluor® fluorescent dyes available from Life Technologies Corp. These dyes are numbered according to their excitation maxima. Other labels that can used also include fluorescein and derivatives such as fluorescein isothiocyanate (FITC) as well as pentafluorophenyl esters (PFP), tetra fluorophenyl esters (TFP), DyLight Fluor® produced by Dyomics, sulforhodamine B, coumarin, eosin, hydroxycoumarin, aminocoumarin, methoxycoumarin dabcyl, dabcyl, Cascade Blue, Lucifer Yellow, P-phycoerythrin, R-phycoerythrin, cyanine 3, cyanine 5, cyanine 7, PE-cyanine 5 conjugates, PE-cyanine 7 conjugates, APC-cyanine 7 conjugates, Red 613, boron-dipyrromethene (Bodipy), lissamine, rhodamine B, peridinin CP, Texas Red, allophycocyanin (APC), TruRed, Oregon Green, tetramethylrhodamine (TRITC), dansyl, dansyl aziridine, Indo-1, Fura-2, (N-(3-triethylammoniumpropyl)-4-(4-(dibutylamino) styryl) pyridinium dibromide) (FM 1-43), 1,1'-dioctadecyl-3,3,3',3'-tetramethylindocarbocyanine perchlorate (DiLC18(3)), Fluo-3, dichlorofluorescin (DCFH), dihydrorhodamine (DHR), seminaphtharhodafluor (SNARF), monochlorobimane, calcein, N-(7-nitrobenz-2-oxa-1,3-diazol-4-yl) amine (NBD), ananilinonapthalene, deproxyl, phthalamide, amino pH phthalamide, dimethylamino-naphthalenesulfonamide, and biotin labels.

Other useful functional molecules include those that display fluorescence resonance energy transfer (FRET). Many such donor-acceptor pairs are known, and include fluorescein to rhodamine, and coumarin to fluorescein or rhodamine. Still another class of useful label pairs includes fluorophore-quencher pairs in which the second group is a quencher, which decreases the fluorescence intensity of the fluorescent group. Some known quenchers include acrylamide groups, heavy atoms such as iodide and bromate, and nitroxide spin labels such as TEMPO.

Methods for labeling specific amino acids with specific reactive fluorophores are known in the art. Examples that can be used in the present invention include but are not limited to:

1) Fluorophores with aldehydes, succinimidyl esters (NHS-esters), tetrafluorophenyl esters (TFP-esters), sulfodichlorophenol ester (SDP-ester), and isocyanates that selectively label the primary amines in lysine amino acids;
2) Fluorophores with maleimides, haloacetimide, bromomethyl, or alkyl halide groups that can react with thiols in cysteine. Maleimide is preferred for its specificity;
3) Cross-linkers with the above groups can be conjugated to amines or thiols and can contain other orthogonal reactive groups that can then be subsequently reacted with fluorophores. For example, one could react a heterobifunctional linker containing an NHS-ester and a handle for click-chemistry (such as an alkene or an azide). This could be reacted with a lysine and then the click-chemistry handle could be reacted with a fluorophore (containing an azide or alkene).

These compounds are commercially available for labeling antibodies (e.g., as used in immunofluorescent staining of cells and tissues) or for labeling proteins for 2D gel electrophoresis prior to mass spectrometry.

Figure 4:
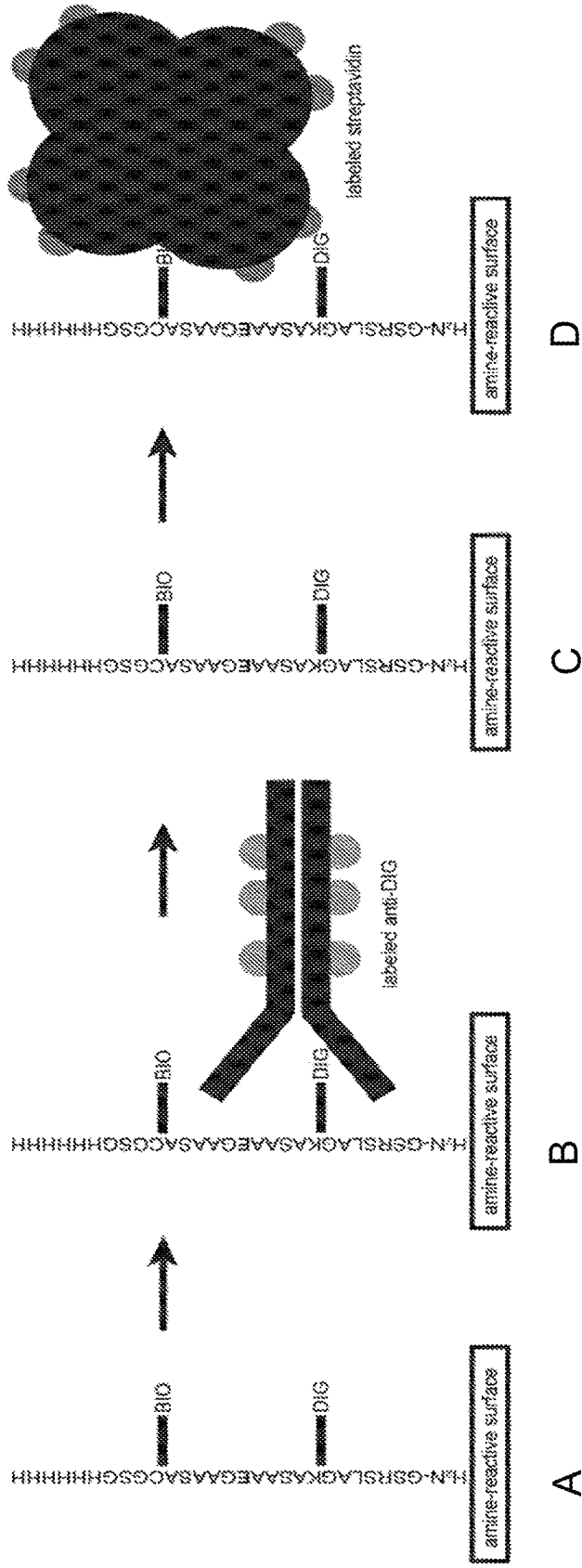
FIG. 4 is a schematic depicting single molecule amino acid identification by sequential labeling with multiply-labeled fluorescent affinity probes.

Another method for labeling is the use small nanoparticles like gold or quantum dots that are functionalized with amine- or thiol-reactive groups to react with the lysine or cysteine amino acids. Thus, a further embodiment of the present method involves labeling the peptides with smaller, affinity tags that are non-fluorescent but can be detected by introduction of labeled antibodies (Examples 6 and 7). The schematic of this method is shown in FIG. 4. There are several advantages to this method. The ability to use multiply-labeled antibodies or brighter luminescent probes such as quantum dot-antibody conjugates leads to improved signal-to-noise in the peptide identification assay. Additionally, because these brighter probes can be introduced to a sample and then reversibly removed, differently colored fluorophores need not be present in the sample at the same time, eliminating complications with fluorophore interactions, such as quenching through energy or electron transfer. Finally, because the affinity tags used for direct labeling of peptides are smaller than fluorophores, covalent coupling can be accomplished with higher efficiency. Affinity tags that can be used in the methods and assays of the present invention include but are not limited to biotin, digoxigenin, hexhistadine, pentahistadine, hemagglutinin (HA-tag), FLAG-tag, myc-tag, and fluorescein.

As shown in FIG. 4, the peptide is first labeled with amino acid-specific affinity tags (biotin and digoxigenin in this case). The immobilized peptide is then probed sequentially, allowing detection of amino acid content by single molecule microscopy. First, multiply-labeled anti-digoxigenin is introduced to detect the presence of digoxigenin-labeled lysine residues. The antibody is then denatured before multiply-labeled streptavidin is introduced to detect the presence of biotin-labeled cysteine residues.

In both labeling embodiments, the peptides would be further digested with endopeptidases and further imaging performed.

Thus, after labeling, the next step is to introduce an amino acid-specific endopeptidase which cleaves the peptides at particular residues. One example of such an endopeptidase is peptidyl-asp metaplo-endopeptidase or AspN, which cleaves peptides at aspartic acid residues. As a result, any labeled residues on the C-terminal side of aspartic acid will disappear, which will be evident when the peptide surface is imaged a second time. A second amino acid-specific endopeptidase such as glutamyl endopeptidase, or GluC, which cleaves at glutamic acid residues can be introduced and a third image is acquired. These three images provide course-grained sequence information about each labeled tryptic peptide associated with each target protein molecule.

In one embodiment, cysteine and lysine residues can labeled with differently colored reactive fluorophores in order to immediately determine the cysteine and lysine content of each peptide by imaging them with a single molecule fluorescence microscope (Examples 2 and 5). This method is illustrated in FIG. 3. A tryptic peptide obtained from a protein digested with trypsin is immobilized on the amine-reactive surface. This tryptic peptide has the amino acid sequence from N-terminal to C-terminal of N-G-I-E-G-L-A-V-K-I-A-V-D-L-N-A-C-R (SEQ ID NO: 1). Cysteine (C) and lysine (K) residues are labeled in two different colors. An image is taken.

The tryptic peptide is then digested with AspN, which cleaves at the Asp (D) residues. A second image is taken.

The peptide is then digested with GluC which cleaves the peptide at glutamic acid residues (E). A third image is taken.

By comparing these three images, the following can be learned about the amino acid sequence of the peptide: it has R at the C-terminal; it contains C and K as well as D between C and K; the C is C-terminal to the K; and it contains E between K and its N-terminal.

Endopeptidases other than AspN and GluC can be used to create alternative or additional peptide fragments from the protein. These endopeptidases include but are not limited to trypsin; chymotrypsin which is specific for the C-terminal side of hydrophobic residues such as leucine, alanine and aromatic amino acids; pepsin; endopeptidase LysN; endopeptidase LysC, specific to the C-terminal side of lysine; and clostripan, specific for the C-terminal side of arginine.

Additionally, chemicals that cleave peptide bonds at particular locations can also be used in the method and include but are not limited to cyanogen bromide, specific for the C-terminal side of methionine; 2-nitro-5-thio-cyano-benzoic acid, specific for the N-terminal side of cysteine; o-iodosobenzoic acid, specific for the C-terminal side of tryptophan and tyrosine; dilute acid, specific for asparagine and proline; and BNPS-skatole, specific for tryptophan.

In principle, the combination of this course-grained sequence information from every labeled tryptic peptide that originates from an individual protein molecule is sufficient, in the case of the human proteome, to uniquely identify 80-90% of proteins depending on the exact imaging scheme by use of computer databases such as the Human Protein Reference Database. A series of computer simulations demonstrated the ability of this single molecule protein identification assay to uniquely identify members of the human proteome (Example 1 and FIG. 5).

While these simulations show that this method accurately identifies most proteins, it is possible to employ an even more sophisticated scheme for fluorescence quantification, using methods such as measuring the lysine-to-cysteine ratio or estimating the absolute number of fluorophores. One such approach to fluorescence quantification is photobleaching. Using a microscope with single molecule sensitivity, photobleaching of a small number of individual fluorophores appear as discrete steps in a temporal recording of fluorescence intensity. For example, if there are three fluorophores in a diffraction spot that are photobleached by laser excitation, a temporal recording of their fluorescence intensity will contain three discrete and abrupt events in which the fluorescence intensity of the spot decreases.

EXAMPLES

The present invention may be better understood by reference to the following non-limiting examples, which are presented in order to more fully illustrate the preferred embodiments of the invention. They should in no way be construed to limit the broad scope of the invention.

Example 1—Computer Simulation

For a given protein sequence, the entire process of tryptic digestion, N-terminal capture, lysine/cysteine labeling, and AspN/GluC digestion was conducted on a computer, and results were compared to a protein sequence database in an attempt to identify the target protein based on the simulation.

Each protein in the database was assigned a code based on the expected single peptide data. Simulations were conducted using a human proteome library consisting of 19,653 protein sequences from the Human Protein Reference Database. The results shown in FIG. 5 were stringent, focusing mainly on unique, perfect matches and associated error rates under a variety of conditions. In addition, the simulation underestimates the amount of information available from experimental data. For example, it does not include information about known or otherwise measurable cleavage site errors or sequence context-dependent inefficiencies that have been characterized previously for specific endopeptidases. Furthermore, in the simulations from Figure 5A, only a digital readout was allowed with no quantification of fluorescence intensity employed. The simulation only recorded a change in signal from fluorescent labels if all of the labels of a given color (e.g., cysteine or lysine) were removed by the cleavage reagent.

Figures 5, 5A, 5B:
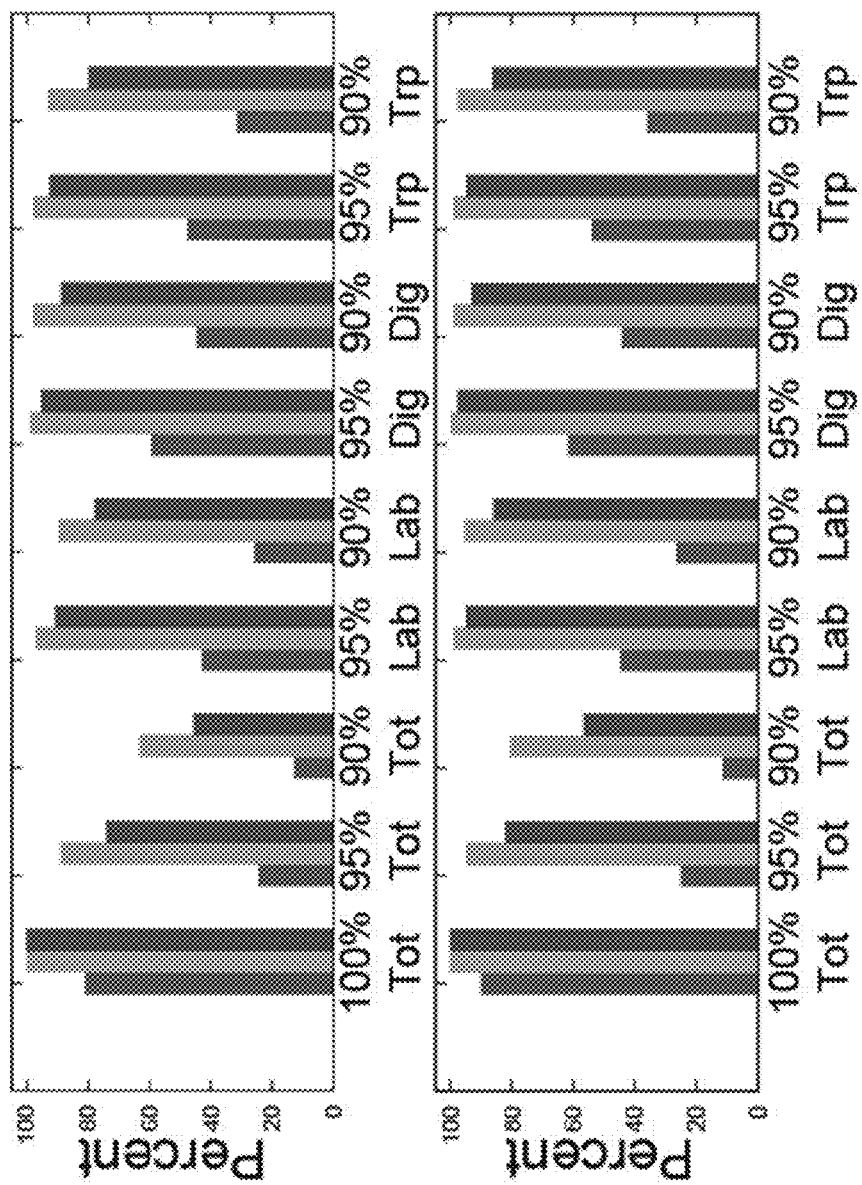
FIG. 5 are graphs showing the results of the human proteome protein identification simulation.
FIG. 5A shows results when using a purely digital fluorescence readout (i.e. no quantification of intensity). The percent unique matches (dark gray, left side), associated accuracy (light gray, middle), and percent of proteins where the correct protein is found (dark gray, right side) is shown in the graph. Several conditions were simulated: 100%/95%/90% efficient trypsinization, labeling/detection, AspN/GluC digestion (marked as "Tot" in FIG. 5); 95/d90% efficient labeling/detection with 100% efficient trypsinization and AspN/GluC digestion (marked as "Lab" in FIG. 5); 95/d90% efficient AspN/GluC digestion with 100% efficient trypsinization and labeling/detection (marked as "Dig" in FIG. 5); and 95%/90% efficient trypsinization with 100% efficient Aspn/GluC digestion and labeling and detection (marked as "Trp" in FIG. 5).
FIG. 5B shows the results of an experiment using the same parameters as in FIG. 5A but with a three-level fluorescence readout.

A variety of conditions were simulated including:
- 100%/95%/90% efficient trypsinization, labeling/detection, AspN/GluC digestion (marked as "Tot" in FIG. 5);
- 95%/d90% efficient labeling/detection with 100% efficient trypsinization and AspN/GluC digestion (marked as "Lab" in FIG. 5);
- 95%/90% efficient AspN/GluC digestion with 100% efficient trypsinization and labeling/detection (marked as "Dig" in FIG. 5);
- 95%/90% efficient trypsinization with 100% efficient AspN/GluC digestion and labeling/detection (marked as "Trp" in FIG. 5).

When each process is 100% efficient, a purely digital readout allows unique identification of 81% of the human proteome. FIG. 5A provides a detailed assessment of how the unique match rate (dark gray bars at left) and the unique match accuracy (light gray bars in middle) change under different conditions. In cases where there was not a unique match, the dark gray bar at the right indicates the percentage of proteins for which the correct protein appears in the list of possible matches.

Figure 5B provides the same information as FIG. 5A for simulations in which a three-level fluorescence quantification is allowed. When images were analyzed for a given peptide, if the fluorescence level decreased after digestion but did not fully disappear, that information was used. For example, if a peptide contained two cysteines prior to digestion with AspN and one cysteine afterwards, that change would be recorded (it would not be recorded in the case of the digital readout used in FIG. 5A). In most cases, this extra information contributed to a higher identification rate with approximately 90% unique identification for the 100% efficiency scenario.

The simulations showed that the most critical parameter is labeling/detection efficiency. In addition, the most significant effect of using a three-level fluorescence readout was the increased accuracy with which unique protein identifications were assigned. In practice, it may be possible to employ an even more sophisticated scheme for fluorescence quantification (e.g. measuring the lysine-to-cysteine ratio or even estimating the absolute number of fluorophores).

Example 2—Generation of Labeled Fluorescent Peptides

A peptide with the sequence GSRSLAGKASAAE-GAASACGSGHHHHHH (SEQ ID NO: 3) was purchased from GeneScript. The peptide was N-terminally acetylated. The peptide was diluted to a final concentration of 400 uM in water. 14 uL of the peptide was added to 14 uL of phosphate buffered saline. To this mixture, tetramethylrhodamine-maleimide (Anaspec) (which reacts with cysteine residues) was added to a final concentration of 1 mM and incubated for two hours at room temperature. The lysine was then acetylated by incubation with sulfo-NHS-acetate at a final concentration of 10 mM for one hour at room temperature. The labeled peptide was then purified on a Ni-NTA spin column (Qiagen) using the C-terminal His-Tag.

For labeling the peptide with two fluorophores (dual-labeling), the peptide was diluted to 360 uM in water and added to 15 uL of phosphate buffered saline. A 20 uL solution of 2 mM tetramethylrhodamine-maleimide (Anaspec) in DMSO (Life Technologies) was added to the peptide solution and incubated at room temperature for 12 hours. At this point, 6 uL of 600 mM sodium borate buffer was added to the solution, bringing it to a pH of 8.5. The mixture was then added to 100 ug of AlexaFluor 647-NHS (Life Technologies) (which reacts with the lysines) and incubated for two hours at room temperature. The two fluorophores labeled at cysteine and lysine, respectively. Remaining unreacted primary amines on lysine residues were quenched by reaction with sulfo-NHS-acetate at a final concentration of 10 mM for one hour at room temperature. Unreacted fluorophores were removed by purifying the peptide on a Ni-NTA spin column (Qiagen) using the C-terminal His-Tag.

For both peptides, the N-terminal acetylated residue was removed by incubation with trypsin (0.1 uM in phosphate-buffered saline for 4-6 hours at 37° C.), which cuts the peptide at arginine. The trypsin does not cleave the peptide at lysines because they are labeled with a fluorophore.

Example 3—Solution-Phase Fluorescent Detection of Sequence-Specific Peptide Digestion Materials and Methods A digestion-free control sample was generated by combining 5 uL of GluC Reaction Buffer (New England BioLabs), 3 uL of 9.2 uM the dual-labeled peptide from Example 2, and 2 uL of nuclease-free water. A digestion reaction mixture was generated containing 25 uL of GluC Reaction Buffer (New England BioLabs), 15 uL of the dual-labeled peptide, and 10 uL of nuclease-free water. This reaction mixture was added to 50 ug of solid GluC endoproteinase (New England BioLabs) on ice. The final concentrations of GluC and peptide were 33.5 uM and 2.8 uM, respectively. From this master mix, five aliquots (10 uL each) were generated and incubated at 37° C. The digestion reaction was stopped after 10 minutes, 30 minutes, 1 hour, 2 hours, and 6 hours by combining one aliquot at each time point with 10 uL of Tricine Sample Buffer (Bio-Rad Laboratories) and placing the quenched sample at 4° C. The digestion-free control and the five quenched reaction mixtures were electrophoresed on a 10-20% Mini-PROEAN Tris-Tricine Precast Gel (Bio-Rad) for one hour at 140V. The gel was illuminated with a UV lamp and imaged with a digital camera. Red channel intensity was used for quantification in FIGS. 6A and B.

Results

Figure 6A:
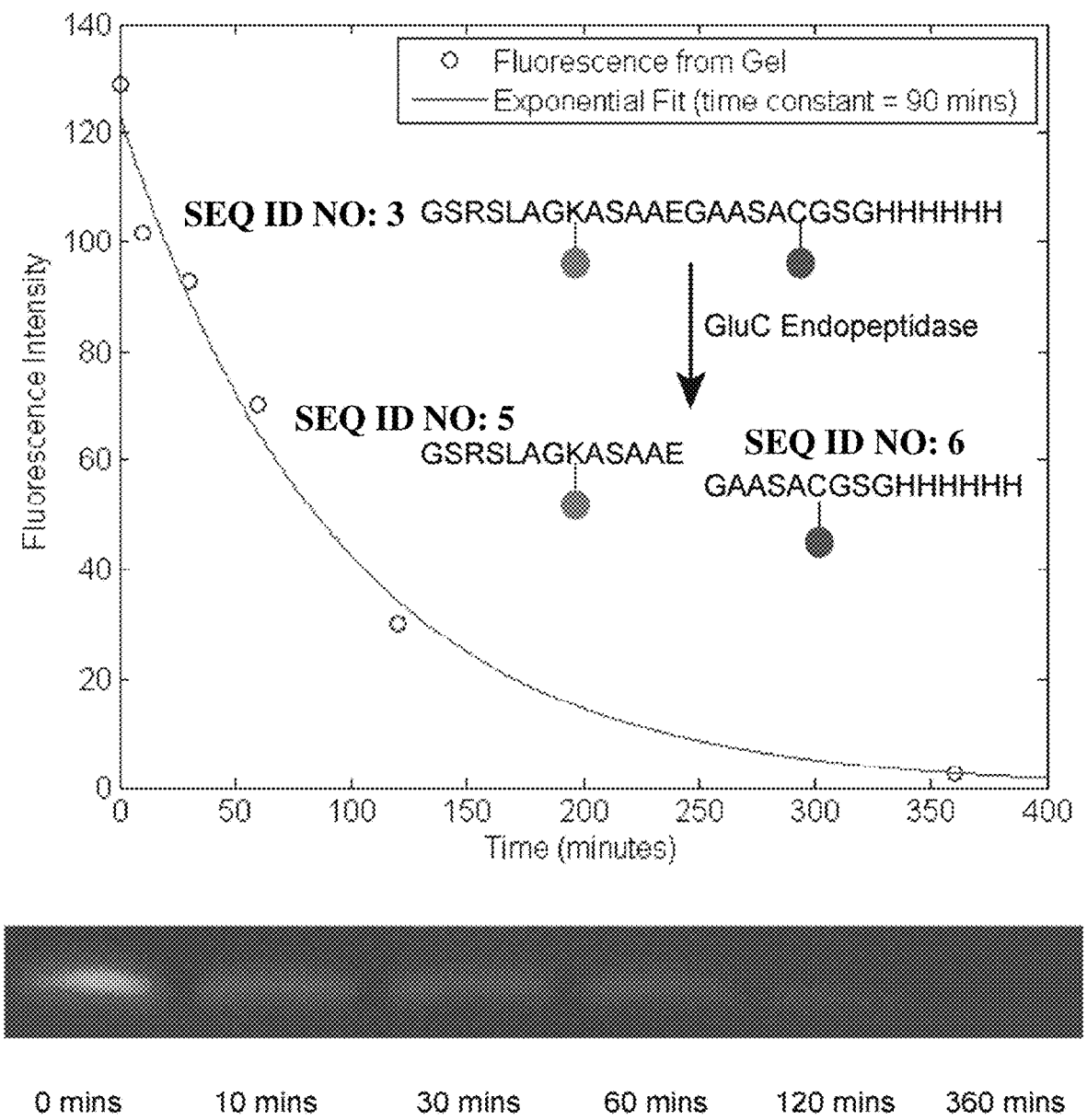
FIG. 6A shows the results of bulk, solution phase kinetics of GluC endopeptidase digestion of a dual-labeled peptide as measured using fluorescence imaging of a gel. A time constant of 90 minutes was detected.

As shown in FIG. 6A, there was progressive signal decay over the course of five hours, corresponding to the activity of the GluC enzyme. The integrated fluorescence intensity of each band in the gel was plotted as a function of time in FIG. 6A, revealing a single exponential decay with a time constant of 90 minutes.

Example 4—Solid-Phase Fluorescent Detection of Sequence-Specific Peptide Detection Materials and Methods To further demonstrate this approach to sequence-specific fluorescence detection in the solid-phase, the experiment in Example 3 was repeated with the fluorescently-labeled peptide immobilized on a latex bead. The bead was functionalized with an aldehyde capture surface, mimicking microfluidic surface chemistry.

A 10 uL solution of 4-5 pM, 3.1 micron diameter aldehyde/sulfate-functionalized latex beads (Life Technologies) was pelleted by centrifugation. A 100 uL solution containing 1 M sodium chloride, 58 nM dual-labeled peptide, and Cyanoborohydride Coupling Buffer (Sigma) was added to the beads. The mixture was incubated for 12 hours at room temperature to allow the N-terminal amine on the labeled peptide to react with aldehydes on the bead surface. The beads were then washed by centrifugation in water and re-suspended in 100 uL of 10% (v/v) ethanolamine in Cyanoborohydride Coupling Buffer (Sigma) to quench unreacted aldehydes. The beads were washed by centrifugation three times to remove unlabeled peptides and ethanolamine and re-suspended to a final concentration of 250 fM in phosphate-buffered saline.

A baseline bead intensity was measured by imaging the labeled peptide-coated beads on a fluorescence microscope (Nikon Ti-U epifluorescence microscope, 20×0.75 NA objective, 532 nm laser excitation, Andor iXon 897 EM-CCD camera). A sample of the beads was pelleted by centrifugation and re-suspended to a final concentration of 60 fM in GluC Reaction Buffer with 1 mg/mL GluC endopeptidase (New England BioLabs). The beads were imaged on a fluorescence microscope to measure average fluorescence intensity at several time points over a seven hour period.

Results

Figure 6B:
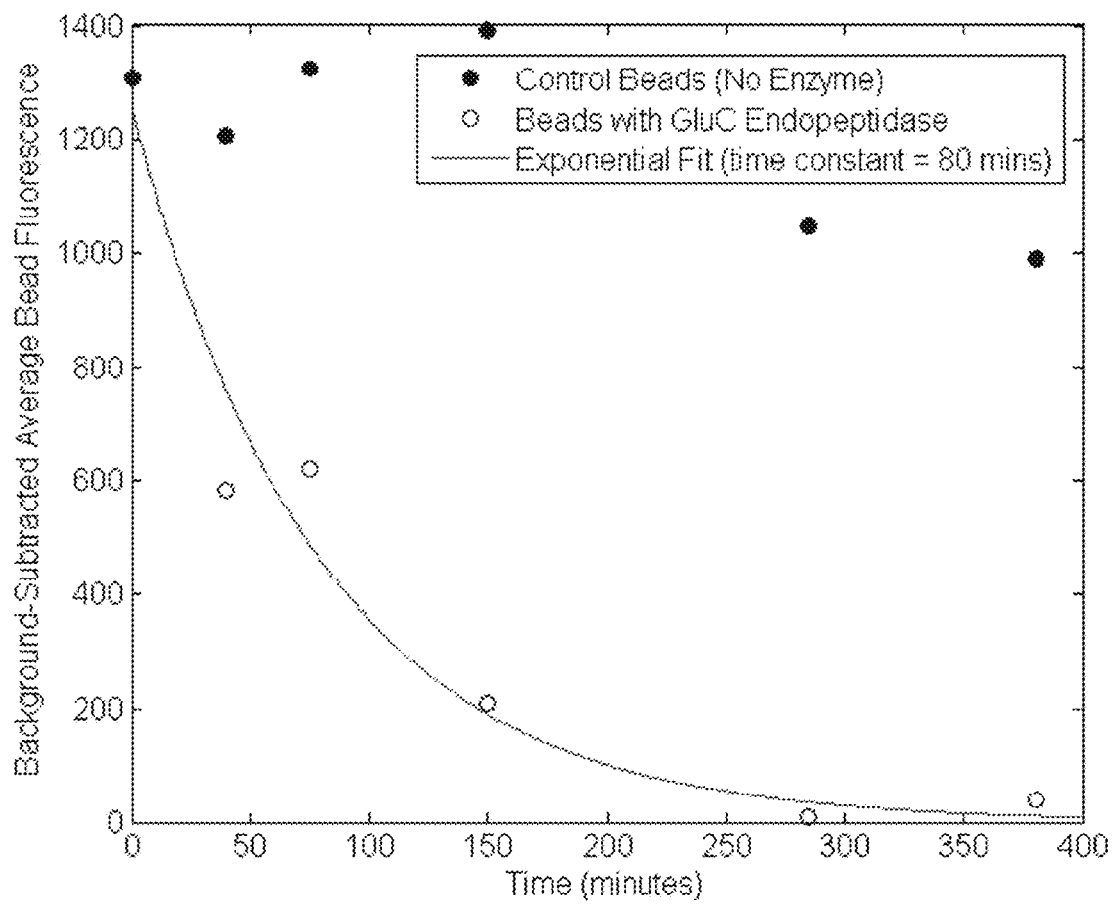
FIG. 6B shows the results of bulk, solid-phase kinetics of GluC endopeptidase digestion of a dual-labeled peptide as measured using fluorescence imaging of a capture bead. The bead was functionalized with an aldehyde capture surface, mimicking microfluidic surface chemistry, and the digestion of immobilized peptide resulted in loss of fluorescence at a similar time constant as measured in FIG. 6A.
Figure 6B:
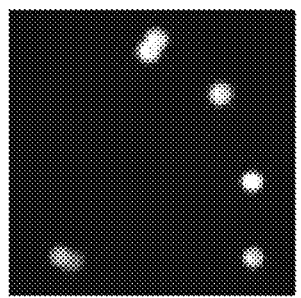
Figure 6B:
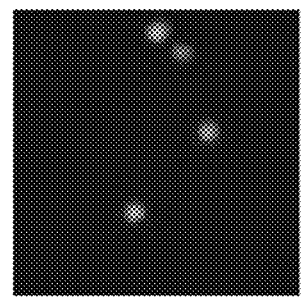

Similar to Example 3, the solution-phase experiment, the fluorescence signal associated with the beads decayed exponentially over time with a similar time constant to what was observed in solution (FIG. 6B). In addition, a set of peptide-linked beads that were not treated with GluC did not exhibit a characteristic exponential decay (FIG. 6B).

Example 5—Sequence-Specific Peptide Detection at the Single Molecule Level

Materials and Methods

Glass coverslips were functionalized with aldehydes by first treating them with air plasma for five minutes (Harrick plasma cleaner), Immersing them in a solution containing 0.5% (v/v) trimethoxysilane aldehyde (United Chemical Technologies) in acidic ethanol (90% 200-proof ethanol, 10% pH 3.5 acetic acid solution) for 15 minutes at room temperature. The coverslips were then immersed in ethanol for 30 seconds, dried with compressed air, and heat-cured at 90° C. for 10 minutes.

Flow cells were fabricated using an aldehyde-functionalized glass coverslip, double-sided tape (Grace Bio-Labs), and polydimethylsiloxane (PDMS) as described in Sims et al. (2011). A 2.5 nM solution of singly-labeled-peptide containing 1% sodium dodecyl sulfate and 0.1% tween-20 was generated in Cyanoborohydride Coupling Buffer. The solution was heated for 2-3 minutes at 95° C. to break peptide aggregates and introduced to each of two flow cells. Following a 12 hour incubation at room temperature, the flow cells were rinsed with 1 mL of phosphate buffered-saline containing 1% sodium dodecyl sulfate and 0.1% tween-20 and then with phosphate buffered-saline containing 0.1% tween-20 to remove unbound peptide. A 200 uL solution of 10% (v/v) ethanolamine in Cyanoborohydride Coupling Buffer was introduced to each flow cell and incubated for 30 minutes at room temperature. The flow cells were then rinsed with 1 mL of phosphate-buffered saline and 0.1% tween-20 to remove ethanolamine.

Ten images of each flow cell were then acquired using a total internal reflection fluorescence (TIRF) microscope (Nikon Ti-U epifluorescence microscope, 60×1.49 NA objective, 532 nm laser excitation, Andor iXon 897 EM-CCD camera) to quantify the number of fluorescently-labeled individual peptide molecules bound to the surface (FIGS. 7A,C). A 100 uL solution of GluC Reaction Buffer was introduced to each flow cell and then 50 uL of 1 mg/mL GluC endoproteinase in GluC Reaction Buffer was introduced to one of the two flow cells. The two flow cells were incubated at 37° C. for 5 hours and then rinsed with 2 mL of phosphate-buffered saline with 0.1% tween-20. Ten images of each flow cell were then acquired using a TIRF microscope (FIGS. 7B,D).

Result

FIG. 7A contains an image corresponding to the median observed number of single molecules observed across multiple fields-of-view prior to GluC introduction, and FIG. 7B contains an image corresponding to the median observed number of single molecules observed after GluC introduction. The concentration of peptide molecules on the surface is approximately 73% lower at this point in the digestion reaction.

FIG. 7C shows an image in the control flow cell that corresponds to the median number of single molecules observed at the beginning of the incubation period. No GluC was added to this flow cell, and the image of the surface in FIG. 7D taken after incubation shows a similar peptide concentration on the surface.

These figures together show significantly more loss of labeled peptide molecules in the GluC-treated flow cell than in the untreated flow cell.

Taken together, these data show that GluC activity can be detected at the single molecule level on the peptide capture surface. GluC was specific to glutamic acid residues and the fluorescent label was specific to cysteine residues. The fluorescence images implied coarse-grained sequence information because the cysteine must be located C-terminal to the cleaved glutamic acid residue in order for digestion to result in removal of the cysteine label.

Example 6—Generation of a Peptide with Multiple Affinity Tags

A peptide with the sequence GSRSLAGKASAAGAASACGSGIIHHHHH (SEQ ID NO: 4) was purchased from GeneScript. The peptide was N-terminally acetylated. The peptide was diluted to a final concentration of 36 uM in phosphate buffered saline (PBS). To this solution, 3 uL of 100 mM maleimide-PEG2-biotin (Pierce) in DMSO was added. The reaction mixture was incubated at room temperature for 12 hours for saturation labeling of the cysteine residues in the peptide sample. 30 uL of 10× sodium borate buffer was added bringing the solution to a pH 8.5. To this mixture, 50 uL of 3 mM digoxigenin-NHS (Sigma) in DMSO was added. The reaction mixture was incubated for 2 hours at room temperature for saturation labeling of the lysine residues in the peptide sample and quenched by addition of 67 uL of 10 mM sulfo-NHS-acetate.

The quenching reaction was incubated at room temperature for one hour. The resulting labeled peptide was then purified on a His-Tag spin column (Qiagen). The N-terminal acetylated residue was then removed by digestion with 0.1 uM trypsin (New England BioLabs) in PBS for six hours at 37° C., and the resulting peptide was re-purified on a His-Tag spin column (Qiagen).

Example 7—Single Molecule Amino Acid Identification Experiment

Materials and Methods

Glass coverslips were functionalized with aldehydes as described in Example 5 and a PDMS flow cell was fabricated on the functionalized coverslip. A 0.5 nM solution of a mixture of biotin/digoxigenin-labeled peptides was introduced to the flow cell in Cyanoborohydride Coupling Buffer (Sigma) supplemented with 0.1% tween-20 and 1% sodium dodecyl sulfate (SDS). The solution was incubated with the functionalized surface for 30 minutes at room temperature. The flow cell was then rinsed with 1 mL of Wash Buffer (PBS containing 1% SDS and 0.1% tween-20) to remove unbound peptide. A 200 uL solution of 10% (v/v) ethanolamine in Cyanoborohydride Coupling buffer (Sigma) was introduced and incubated for 30 minutes at room temperature to quench any unreacted aldehydes on the surface. The flow cell was rinsed with 1 mL of Wash Buffer before the introduction of 500 pM rhodamine-labeled anti-digoxigenin antibody (Fisher) and incubated for 20 minutes. After rinsing the flow cell with Wash Buffer, the surface was imaged using the TIRF microscope described in Example 5 with 532 nm laser excitation. A solution of 2M guanidinium isothiocyanate was then introduced to the flow cell to denature and remove the anti-digoxigenin. After rinsing the flow cell with 1 mL of Wash Buffer, a solution containing 5 nM AlexaFluor 647-labeled streptavidin was introduced in Wash Buffer and incubated for 20 minutes. After rinsing the flow cell with Wash Buffer, the surface was imaged with 637 nm laser excitation.

Peptides with three different sequences were used:

```
                                              (SEQ ID NO: 3)
GSRSLAGKASAAGAASACGSGHHHHHH
(with a lysine and cysteine residue in bold)

(SEQ ID NO: 4)
GSRSLAGKASAAGAASAKGSGHHHHHH
(with two lysine residues in bold)

(SEQ ID NO: 5)
GSRSLAGKASAAGAASACGSGHHHHHH
(with two cysteine residues in bold).
```

The peptides were used in a mix of 50% of the peptide with SEQ ID NO: 4 and 25% each of the peptide with SEQ ID NOs 5 and 6.

Result

Figure 8:
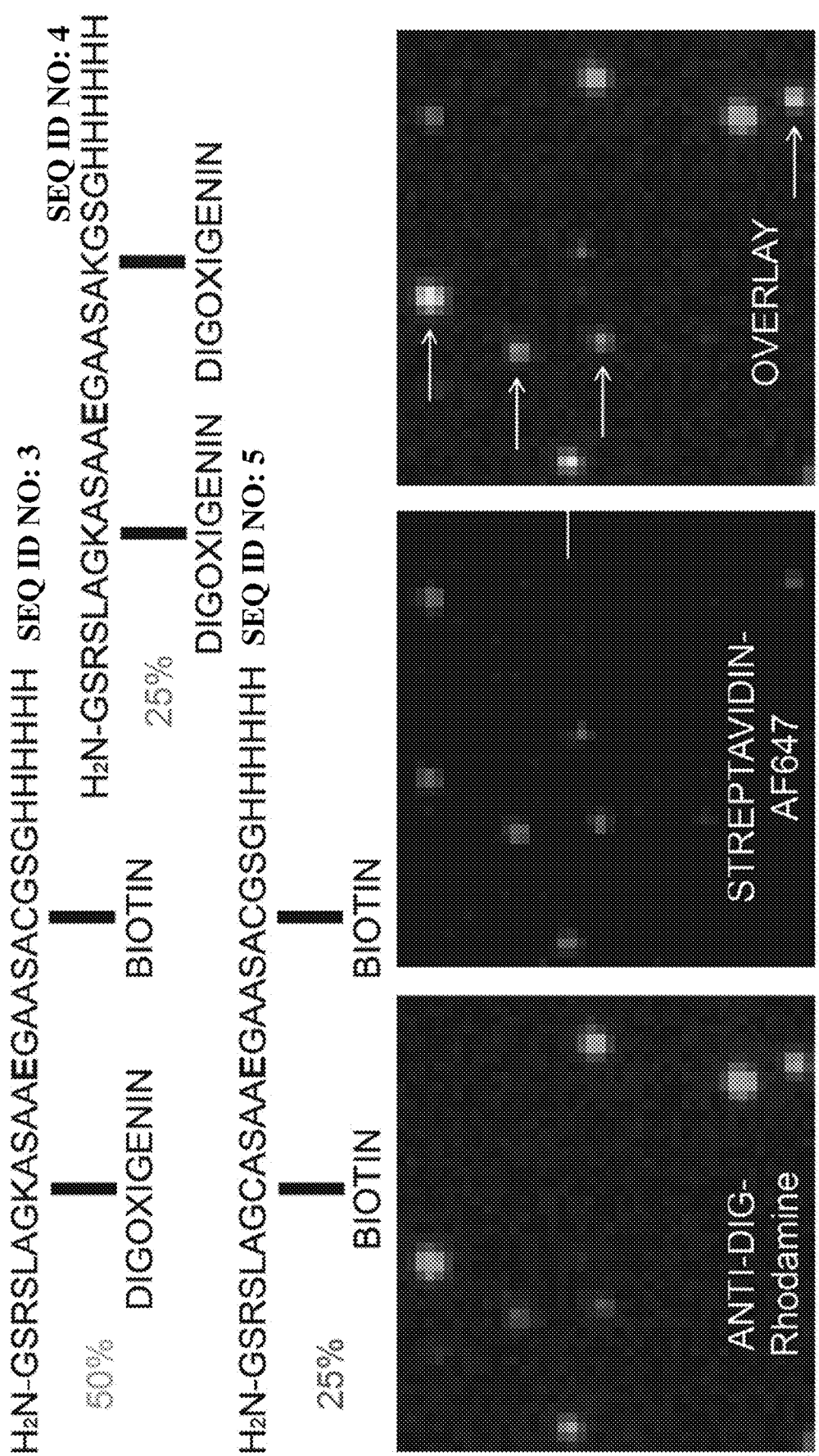
FIG. 8 shows the results of a single molecule determination of amino acid content in a mixture of peptides using the sequential fluorescent probing scheme

FIG. 8 shows two-color fluorescence images of sequential labeling experiments. The first panel on the left hand side shows the peptides containing anti-digoxin labeled cysteines. The middle panel shows the peptides containing streptavidin labeled lysines. The right hand panel shows the overlay of the two images. The peptides in the overlay which are denoted by arrows contain both cysteine and lysine, and represent about half of the number of images, in agreement with the amount of peptide with each sequence (SEQ ID NO: 4, 5, or 6) used.

REFERENCES

Abate et al. (2010) *PNAS* 107:19163
Men et al. (2012) *Analytical Chemistry* 84:4262
Sims et al. (2011) *Nature Methods* 8:575

The invention claimed is:

1. A method for identifying a protein in a sample, comprising:

A. introducing at least one protein molecule onto a bead, and wherein the bead contains an amine-reactive surface and wherein the amine-reactive surface allows for direct reaction between the surface and the N-termini of a peptide and the protein molecule has been treated such that the N-terminals are capable of reacting to the amine-reactive surface;

B. incubating an endopeptidase with the at least one protein molecule on the bead for a time and under conditions which allow the endopeptidase to cleave the protein into peptides, wherein the endopeptidase cleaves the at least one protein molecule at specific amino acids in the protein resulting in peptides comprising an N-terminal amino acid and corresponding to the at least one protein molecule contained on the bead;

C. allowing the peptides to react via their N-terminal amino acid residue with the amine-reactive surface of the bead, for a time and under conditions which result in the peptides attaching to the amine-reactive surface of the bead and forming a pattern on the amine-reactive surface, wherein the pattern is associated with the bead containing the at least one protein molecule;

D. washing the endopeptidase from the bead, wherein the washing of the endopeptidase ends the cleaving of the protein in step B;

E. labeling the peptides at specific amino acid residues, such that the specific amino acid residues can be detected when imaged;

F. imaging the peptides to detect the labeled amino acids and generating amino acid sequence information from the peptides in step B;

G. further incubating the peptides generated in step B, with at least one enzyme or chemical for a time and under conditions which allow the enzyme or chemical to cleave and imaging the resulting peptides to generate additional amino acid sequence information;
H. washing the enzyme or chemical from the bead, wherein the washing of the enzyme or chemical ends the cleaving of the peptides in step G;
I. further labeling the peptides generated in step G, at specific amino acids different from the label in step E:
J. imaging the peptides to detect the labeled amino acids and generating additional amino acid sequence information; K. compiling the generated amino acid sequence information from steps F, G and J to obtain a putative amino acid sequence of the at least one protein molecule;
L. comparing the putative amino acid information of at least one protein molecule with a known amino acid sequence of proteins; and
M. identifying the protein from the comparison in step L; wherein steps G.-J. are repeated with a plurality of enzymes or chemical and labels as desired until a putative amino acid sequence of the at least one protein molecule is obtained.

2. The method of claim 1, wherein the bead is made from a material chosen from the group consisting of latex and silicon.

3. The method of claim 1, wherein the endopeptidase used in step B. is selected from the group consisting of trypsin, chymotrypsin, elastase, thermolysin, pepsin, clostripan, glutamyl endopeptidase (GluC), endopeptidase ArgC, peptidyl-asp metallo-endopeptidase (ApsN), endopeptidase LysC and endopeptidase LysN.

4. The method of claim 1, wherein the bead is contained in microwells or enclosed in a water-oil emulsion droplet.

5. The method of claim 1, wherein the peptides are labeled with one or more fluorescent dyes.

6. The method of claim 5, wherein the fluorescent dyes are selected from the group consisting of Alexa Fluor®, tetramethylrhodamine-maleimide, fluorescein, fluorescein isothiocyanate (FITC), pentafluorophenyl esters (PFP), tetra fluorophenyl esters (TFP), DyLight Fluor, sulforhodamine B, coumarin, eosin, hydroxycoumarin, aminocoumarin, methoxycoumarin dabcyl, dabcyl, Cascade Blue, Lucifer Yellow, P-phycoerythrin, R-phycoerythrin, cyanine 3, cyanine 5, cyanine 7, PE-cyanine 5 conjugates, PE-cyanine 7 conjugates, APC-cyanine 7 conjugates, Red 613, boron-dipyrromethene (Bodipy), lissamine, rhodamine B, peridinin CP, Texas Red, allophycocyanin (APC), TruRed, Oregon Green, tetramethylrhodamine (TRITC), dansyl, dansyl aziridine, Indo-1, Fura-2, (N-(3-triethylammoniumpropyl)-4-(4-(dibutylamino) styryl) pyridinium dibromide) (FM 1-43), 1,1'-ioctadecyl-3,3,3',3'-etramethylindocarbocyanine perchlorate (DilC18(3)), Fluo-3, dichlorofluorescin (DCFH), dihydrorhodamine (DHR), seminaphtharhodafluor (SNARF), monochlorobimane, calcein, N-(7-nitrobenz-2-oxa-1,3-diazol-4-yl) amine (NBD), ananilinonapthalene, deproxyl, phthalamide, amino pH phthalamide, dimethylamino-naphthalenesulfonamide, and biotin labels.

7. The method of claim 1, wherein the peptides are labeled with affinity tags.

8. The method of claim 7, wherein the affinity tags are selected from the group consisting of biotin, digoxigenin, hexhistadine, pentahistadine, hemagglutinin (HA-tag).

9. A method for identifying a protein in a sample, comprising:
A. labeling the protein at a plurality of specific amino acid residues such that the specific amino acid residues can be detected when imaged;
B. introducing at least one protein molecule from the labeled protein onto a bead wherein the bead comprises an amine-reactive surface which allows for direct reaction between the bead and the N-termini of a peptide and the protein molecule has been treated such that the N-terminals are capable of reacting to the amine-reactive surface;
C. incubating an endopeptidase with the at least one protein molecule on the bead for a time and under conditions which allow the endopeptidase to cleave the at least one protein molecule into peptides wherein the endopeptidase cleaves the at least one protein molecule at specific amino acids in the at least one protein molecule resulting in peptides comprising an N-terminal amino acid and corresponding to the at least one protein molecule contained on the bead;
D. allowing the peptides to react via their N-terminal amino acid residue with the amine-reactive surface of the bead, for a time and under conditions which result in the peptides attaching to the bead and forming a pattern on the amine-reactive surface, wherein the pattern is associated with the bead containing the at least one protein molecule;
E. washing the endopeptidase from the bead, wherein the washing of the endopeptidase ends the cleaving of the protein in step C;
F. imaging the peptides to detect labeled amino acids and generate amino acid sequence information from the peptides in step C;
G. further incubating the peptides generated in step C, with at least one enzyme or chemical for a time and under conditions which allow the enzyme to cleave peptides at specific amino acid residues and imaging the resulting peptides to generate additional amino acid sequence information;
H. washing the enzyme or chemical from the bead, wherein the washing of the enzyme or chemical ends the cleaving of the peptides in step G;
I. compiling the generated amino acid sequence information from steps F and G to obtain a putative amino acid sequence of the at least one protein molecule;
J. comparing the putative amino acid sequence information of the at least one protein molecule with a known amino acid sequence of proteins; and
K. identifying the protein from the comparison in step J; wherein steps G-I are repeated with a plurality of enzymes or chemical as desired until a putative amino acid sequence of the at least one protein molecule is obtained.

10. The method of claim 9, wherein the bead is made from a material chosen from the group consisting of latex and silicon.

11. The method of claim 9, wherein the endopeptidase used in step C is selected from the group consisting of trypsin, chymotrypsin, elastase, thermolysin, pepsin, clostripan, glutamyl endopeptidase (GluC), endopeptidase ArgC, peptidyl-asp metallo-endopeptidase (ApsN), endopeptidase LysC and endopeptidase LysN.

12. The method of claim 9, wherein the bead is contained in microwells or enclosed in a water-oil emulsion droplet.

13. The method of claim 9, wherein the peptides are labeled with one or more fluorescent dyes.

14. The method of claim 13, wherein the fluorescent dyes are selected from the group consisting of Alexa Fluor®, tetramethylrhodamine-maleimide, fluorescein, fluorescein isothiocyanate (FITC), pentafluorophenyl esters (PFP), tetra fluorophenyl esters (TFP), DyLight Fluor, sulforhodamine B, coumarin, eosin, hydroxycoumarin, aminocoumarin, methoxycoumarin dabcyl, dabcyl, Cascade Blue, Lucifer Yellow, P-phycoerythrin, R-phycoerythrin, cyanine 3, cyanine 5, cyanine 7, PE-cyanine 5 conjugates, PE-cyanine 7 conjugates, APC-cyanine 7 conjugates, Red 613, borondipyrromethene (Bodipy), lissamine, rhodamine B, peridinin CP, Texas Red, allophycocyanin (APC), TruRed, Oregon Green, tetramethylrhodamine (TRITC), dansyl, dansyl aziridine, Indo-1, Fura-2, (N-(3-triethylammoniumpropyl)-4-(4-(dibutylamino) styryl) pyridinium dibromide) (FM 1-43), 1,1'-ioctadecyl-3,3,3',3'-etramethylindocarbocyanine perchlorate (DilC18(3)), Fluo-3, dichlorofluorescin (DCFH), dihydrorhodamine (DHR), seminaphtharhodafluor (SNARF), monochlorobimane, calcein, N-(7-nitrobenz-2-oxa-1,3-diazol-4-yl) amine (NBD), ananilinonapthalene, deproxyl, phthalamide, amino pH phthalamide, dimethyl-amino-naphthalenesulfonamide, and biotin labels.

15. The method of claim 9, wherein the peptides are labeled with affinity tags.

16. The method of claim 15, wherein the affinity tags are selected from the group consisting of biotin, digoxigenin, hexhistadine, pentahistadine, hemagglutinin (HA-tag), FLAG-tag, myc-tag, and fluorescein.

17. A kit for identifying a protein in a sample according to the method of claim 1, said kit comprising beads coated with an amine-reactive surface material, reagents to label and detect specific amino acid residues, endopeptidases, and instructions for use.

18. The kit of claim 17, wherein the labels are chosen from the group consisting of fluorescent dyes and affinity tags.

19. The kit of claim 17, further comprising denaturants, buffers, and reagents for coupling the peptides to the amine-reactive surface, and amine-blocked, autolysis-resistant endopeptidases.

* * * * *

UNITED STATES PATENT AND TRADEMARK OFFICE
CERTIFICATE OF CORRECTION

PATENT NO. : 11,927,593 B2
APPLICATION NO. : 16/592245
DATED : March 12, 2024
INVENTOR(S) : Peter Sims It is certified that error appears in the above-identified patent and that said Letters Patent is hereby corrected as shown below:

In the Specification

Column 1, Lines 17-19 read:
"This invention was made with government support under grants 1R21EB016980 and 1K01EB016071 awarded by NIH. The government has certain rights in the invention."
Whereas they should read:
"This invention was made with government support under EB016071, and EB016980 awarded by the National Institutes of Health. The government has certain rights in the invention."

Signed and Sealed this
Twenty-eighth Day of May, 2024

Katherine Kelly Vidal
*Director of the United States Patent and Trademark Office*